United States Patent [19]

Kiyoshige et al.

[11] Patent Number: 4,911,918

[45] Date of Patent: Mar. 27, 1990

[54] ORAL COMPOSITION CONTAINING STABILIZED ANTIBODY

[75] Inventors: Tatsuo Kiyoshige, Hadano; Yasuo Kikuchi, Odawara, both of Japan

[73] Assignee: Lion Corporation, Tokyo, Japan

[21] Appl. No.: 874,124

[22] Filed: Jun. 13, 1986

[30] Foreign Application Priority Data

Jun. 14, 1985 [JP] Japan .................................. 60-129528

[51] Int. Cl.$^4$ .......................... A61K 7/16; A61K 7/28; A61K 39/40

[52] U.S. Cl. ........................................ 424/50; 424/49; 424/87; 514/900; 514/901; 514/902; 514/970

[58] Field of Search ..................... 424/49–50, 424/87; 514/900–902, 970

[56] References Cited

U.S. PATENT DOCUMENTS

| | | | |
|---|---|---|---|
| 4,324,782 | 4/1982 | Beck | 424/87 |
| 4,689,221 | 8/1987 | Kiyoshige | 424/87 |
| 4,693,888 | 9/1987 | Miyahara | 424/57 |
| 4,714,612 | 12/1987 | Nakamura | 424/85.5 |
| 4,725,428 | 2/1988 | Miyahara | 424/50 |

FOREIGN PATENT DOCUMENTS 0025318 2/1984 Japan .
0110626A 6/1984 Japan .
2176400A 12/1986 United Kingdom .

OTHER PUBLICATIONS

J. Abst. J59025–318–A, Jul. 29, 1982 (English Lang. Abst.).
J. Abst. J59110–626A, Dec. 17, 1982 (English Lang. Abst.).

*Primary Examiner*—F. T. Moezie
*Attorney, Agent, or Firm*—Birch, Stewart, Kolasch & Birch

[57] ABSTRACT

An oral composition for preventing periodontal diseases through suppression of the colonization of causative bacteria of periodontal diseases comprises an antibody obtained by immunizing a mammal with at least one antigen selected from the group consisting of periodontal causative bacteria, their pilus and capsule fractions, and aluminum hydroxide for stabilizing said antibody.

15 Claims, No Drawings

ORAL COMPOSITION CONTAINING STABILIZED ANTIBODY

BACKGROUND OF THE INVENTION

This invention relates to an oral composition which can prevent periodontal disease through suppression of the intraoral colonization of the causative bacteria of periodontal diseases such as *Bacteroides gingivalis*. More specifically, it relates to an oral composition which coprises a specific type of antibody obtained by immunizing a mammal with at least one antigen selected from the group consisting of periodontal causative bacteria, their pillus and capsule fractions. The composition ensures the stability of the antibody over a long period of time, so that the efficacy of the antibody is reliably prolonged.

There are many people who have periodontal disease such as gingivitis and periodontitis. The rate of such disease in adults is especially on the increase. Prevention of periodontal diseases will be an important problem in the future for an increasing number of aged persons.

Periodontal disease is primarily caused by bacteria existing in accumulated plaque in periodontal pockets. A healthy periodontal pocket is usually composed of an overwhelming amount of gram positive bacteria, while the amount of gram negative bacteria increases with the progress of the periodontal disease. *Bacteroides gingivalis, Fusobacterium nucleatum, Eikenella corrodens, Actionobacillus actinomycetemcomitans* and so forth are primarily listed as such gram negative bacteria. In the focal regions of adult patients with severe periodontal disease, gram negative bacteria are detected in most cases among which Bacteroides gingivalis is separated in specially high frequency. In many of these cases, the titer of anti-*Bacteroides gingivalis* antibody in the serum of the patient also increases. In addition, it has been demonstrated that the inoculation of an animal with *Bacteroides gingivalis* aggravates periodontal inflammation. These results indicate that *Bacteroides gingivalis* plays an important role in the development of periodontal diseases. *Bacteroides gingivalis* adheres to periodontal mucosa by means of its pili and capsule existing on the surface of its bacterial body, thereby proliferating and badly influencing the periodontal region.

In addition, *Actinomyces viscosus*, which is a gram positive bacterium, is detected from the focal regions of periodontal diseases and is known to be a periodontal causative bacterium.

In order to prevent periodontal diseases, the inhibition of the colonization or suppression of the proliferation of the periodontal causative bacteria such as *Bacteriodes gingivalis* in the mouth is effective and bactericides are now mainly used for that purpose. In some more specific methods, the inhibition of the colonization of the periodontal causative bacteria in the mouth is attempted by using a vaccine. However, since the whole bacterial body is used as an active vaccine directly injected into the living human body in all of these methods, they have problems in terms of both effect and toxicity.

Under these circumstances in the art, we made studies of a highly safe method which can effectively inhibit the colonization of *Bacterides gingivalis* in the mouth to more reliably prevent periodontitis. As a result, we found that an antibody in blood or milk, which was obtained by immunization of mammals with *Bacteroides gingivalis,* its pilus or capsule fraction as an antigen, suppressed the colonization of *Bacteroides gingivalis* in the mouth. Based on the above finding, we proposed an oral composition comprising the antibody (the U.S. patent application Ser. No. 686,904).

However, it was also found that these antibodies could not always be stably kept in the oral composition, along with the problem that the antibodies were liable to be deactivated by the presence of anionic surface active agents such as sodium lauryl sulfate.

SUMMARY OF THE INVENTION

Accordingly, it is an object of the present invention to provide oral compositions which comprise an antibody of the type mentioned above stabilized in the composition, whereby the efficacy of the antibody can be shown over a long term.

It is another object of the present invention to provide oral compositions which can effectively prevent colonization of periodontal causative bacteria in the mouth and thus prevent periodontal diseases such as periodontitis.

It is a further object of the present invention to provide a method for stabilizing an antibody of the type mentioned above in an oral composition.

The above objects can be achieved, according to the present invention, by an oral composition which comprises an effective amount of an antibody, which is obtained by immunizing a mammal with an antigen selected from the group consisting of periodontal causative bacteria, their pilus and capsule fractions, and aluminum hydroxide.

More detailed, in order to obtain an oral composition in which the efficacy of the above-said antibody is exerted even after a long period of storage, we have made further investigations. As the result, it has been found that when the antibody is used in combination with aluminum hydroxide, the deactivation of the antibody can be prevented and thus the antibody can be stabilized in the composition over a long term.

Since aluminum hydroxide is formulated in the composition, the efficacy of the antibody is not lost even though anionic surface active agents such as sodium lauryl sulfate, which tend to deactivate the antibody, are present. Accordingly, when the composition is made up into a dentifrice in which aluminum hydroxide is used example, as a main abrasive, the antibody can be effectively used as an effective ingredient of the dentifrice.

Therefore, since the oral composition contains the antibody stably, the colonization of the periodontal causative bacteria in the mouth is effectively prevented even in the case of application of the oral composition stored for a long period of time, resulting in the prevention of periodontal diseases such as periodontisis.

In addition, since said antibody and aluminum hydroxide are highly safe, the oral composition according to this invention can be safely used.

The above and other objects, features, and advantages of this invention will be more fully understood by reading the following description.

DETAILED DESCRIPTION AND EMBODIMENTS OF THE INVENTION

The oral composition of the present invention comprises as its effective component an antibody which is obtained by immunizing a mammal selected from the group consisting of causative bacteria of periodontal diseases, their pilus and capsule fractions.

The causative bacteria of periodontal diseases used as the antigen include gram negative bacteria such as *Bacteroides gingivalis, Actinobacillus actinomycetemcomitans* and the like, and *Actinomyces viscosus*. As the strains thereof, those isolated from the focal regions of periodontal diseases may be used. The strains supplied by the Forsyth Dental Center in Boston, U.S.A. may also be used.

Whole bacterial bodies of the periodontal causative bacteria may be prepared according to a well known method. For example, *Bacteroides gingivalis* used as an antigen may be prepared by culturing the bacterium in a medium prepared by adding hemin and menadione to Todd-Hewitt broth before the grown bacterium is washed and treated with formalin. Pili and capsules of the periodontal causative bacteria used as antigens may be severed and separated from the bacteria according to the well known method.

The usual method may be adopted in immunizing mammals with said antigens. As mammals to be immunized, rabbits, goats, sheep, horses, cows, etc. may be used.

The antibody (immunoglobulin fractions in the antiserum and the milk) may be separated from the antiserum and the milk according to the ordinary antibody purification method including the salting-out method, the gel-filtration method, ion-exchange chromatography, affinity chromatography, and the like, the salting-out method using ammonium sulfate being preferred. In the salting-out method, the antiserum or the milk is saturated with ammonium sulfate to produce the precipitates, followed by dialyzing the precipitates against physiological saline to obtain the purified precipitates as the antibody. The preferred antibody is obtained from the equine antiserUm and the bovine antiserum and milk.

In the present invention, the antibody contained in the antiserum and milk obtained by immunizing the mammal with said antigen is blended in the composition. In this case, the antiserum and milk as well as the antibody separated and purified from the antiserum and milk may be used. Each of these matters may be used alone or in a combination of two or more.

It is preferred that the amount of the above antibodies administered is 0.0001-50 g/kg/day and that the content of the above antibodies is 0.0002-10% by weight, preferably 0.002-5% by weight of the composition.

The oral composition of the present invention comprises, aside from the antibody, aluminum hydroxide as a stabilizer for the antibody. Aluminum hydroxide can effectively prevent deactivation of the antibody. Even though anionic surface active agents, which tend to deactivate the antibody, are formulated, the antibody can be stably kept over a long term.

Aluminum hydroxide may be any ordinary commercial products. Modified aluminum hydroxide which is obtained by treating aluminum hydroxide with an acid such as phosphoric acid, or a salt thereof may be also used. The aluminum hydroxide is not critical with respect to the average size and is preferred to be in the range of from 1 to 50 μm.

The amount of aluminum hydroxide is from 5 to 70%, preferably from 10 to 55% by weight of the total oral composition.

Aside from the antibody and aluminum hydroxide, the oral composition of the present invention may further comprise at least one synergist selected from fluoride providing compounds, chlorhexidines, lytic enzymes, bacteriocins, proteases, and dextranases. The addition of these synergists can more reliably suppress the colonization of the periodontal causative bacteria in the mouth to effectively prevent periodontal diseases.

Examples of the fluoride compounds include monofluorophosphates such as sodium monofluorophosphate, potassium monofluorophosphate, sodium hydrogen monofluorophosphate, ammonium monofluorophosphate and the like, alkali metal fluorides such as sodium fluoride, ammonium fluoride and the like, potassium hexafluorozirconate, potassium hexafluorotitanate, cesium fluoride, nickel fluoride, zirconium fluoride, silver fluoride, hexylamine hydrofluoride, laurylamine hydrofluoride, cetylamine hydrofluoride, glycine hydrofluoride, lysine hydrofluoride, alanine hydrofluoride and the like, and stannous fluorides such as stannous fluoride and stannous fluorochloride. Of these, monofluorophosphates such as sodium monofluorophosphate, potassium monofluorophosphate and the like, alkali metal fluorides such as sodium fluoride, potassium fluoride, ammonium fluoride and the like, and stannous fluoride such as stannous fluoride and stannous fluorochloride are preferred. Most preferably, sodium monofluorophosphate, sodium fluoride and stannous fluoride are used.

Chlorhexidines include chlorhexidine hydrochloride, chlorhexidine gluconate and the like.

Examples of the lytic enzymes include those derived from *Streptomyces griseus, Streptomyces diastatochromagenes, Streptomyces farinosus*, bacteria belonging to the genus Chalaropsis, the genus Flavobacterium and the genus Myxobacter, *Pseudomonas aeruginosa*, bacteria belonging to the genus Aeromonas, *Streptomyces albus, Streptomyces globiporus*, and the like.

Examples of the bacteriocins include those derived from *Bacteroides melaninogennicus, Enterobactor cloacase, Escherichia coli, Proteus mirabilis, Pseudomonas aeruginosa, Streptococcus mutans, Staphylococcus staphylolyticus*, and the like.

Preferable examples of the proteases include those derived from the genuses Aspergillus sp. and Bacillus sp., and preferable examples of the dextranases include those derived from the genuses Chaetonium sp., Streptomyces sp., Bacillus sp., Corynebacterium and the like.

These synergists may be used singly or in combination of two or more different types of synergists. The antibody and synergists may be mixed together and made up into a desired preparation. Alternatively, the antibody and the synergists may be, respectively, made up into separate preparations and employed in combination on application.

The dosages of the synergists are in ranges of from 0.0001 to 1 g/kg/day, calculated as fluoride, for fluoride compounds, from 0.0001 to 1 g/kg/day, calculated as chlorhexidines, for chlorhexidines, from 0.0001 to 10 g/kg/day for lytic enzymes and bacteriocins, and from 0.0001 to 5 g/kg/day for proteases and dextranases. These synergist ingredients are formulated in amounts, based on the total oral compositions, from 0.001-1%, preferably from 0.01 to 0.5% by weight for fluoride compounds on calculation as fluoride, from 1 to 10000 ppm, preferably from 10 to 500 ppm for chlorhexidines on calculation as chlorhexidines from 0.0001 to 10%, preferably from 0.001 to 5% by weight for each lytic enzymes and bacteriocins, from 0.0001 to 10%, preferably from 0.001 to 5% by weight for proteases, and from 0.0001 to 10%, preferably from 0.001 to 5% by weight for dextranases. The formulated composition is used in the above-defined range of dosage.

The oral composition of the present invention is favorably used as dentifrices such as toothpaste, toothpowder, liquid dentifrice and the like. Moreover, the composition may be made up into various oral preparations. For these purposes, other ingredients necessary for intended purposes and preparations may be added to the oral composition of the invention.

For instance, for the preparation of the dentifrice, it is preferred to use aluminum hydroxide as a main abrasive as set forth before. In addition to aluminum hydroxide, other types of abrasive may be added, including calcium secondary phosphate dihydrate, calcium secondary phosphate anhydride, calcium primary phosphate, calcium tertiary phosphate, calcium carbonate, calcium pyrophosphate, insoluble sodium metaphosphate, amorphous silica, crystalline silica, aluminosilicates, aluminum oxide, magnesium tertiary phosphate, magnesium carbonate, magnesium sulfate, titanium oxide, resins and the like.

For the preparation of paste composition such as toothpastes, binders are generally used in an amount of from 0.3 to 5% by weight of the composition. Examples of the binder include sodium carboxymethyl cellulose, methyl cellulose, sodium carboxymethyl hydroxyethyl cellulose, hydroxyethyl cellulose, sodium alginate, carrgeenan, gum arabic, xanthane gum, gum tragacanth, karaya gum, polyvinyl alcohol, sodium polyacrylate, carboxyvinyl polymer, and polyvinylpyrrolidone. When carrageenan is used, the stability of the antibody can be further improved. The paste composition may further comprise 10 to 70% by weight of a humectant such as, for example, polyethylene glycol, ethylene glycol, sorbitol, glycerine, propylene glycol, 1,3-butylene glycol, xylitol, maltol, lactol and the like.

The oral composition of the present invention may further comprise from 0.1 to 6%, preferably from 0.3 to 3% by weight of anionic, nonionic, cationic and/or amphoteric surface active agents. As set forth before, since aluminum hydroxide is formulated in the composition, the deactivation of the antibody can effectively be prevented if anionic surface active agents are added. Accordingly, there may be added anionic surface active agents such as, for example, water-soluble salts of alkylsulfates whose alkyl group has from 8 to 18 carbon atoms, e.g. sodium laurylsulfate, sodium myristylsulfate and the like, water-soluble higher fatty acid monoglyceride sulfates whose fatty acid group having from 10 to 18 carbon atoms, e.g. sodium laurylmonoglyceride sulfate, sodium coconut oil fatty acid monoglyceride sulfate, sodium higher fatty acid monoglyceride monosulfate and the like, sodium salts of alpha-olefinsulfonates, paraffinsulfonates and sodium N-methyl-N-palmitoyltauride, sodium N-lauroylsarcocinate, sodium N-lauroyl-beta-alanine and the like, of which water-soluble salts of alkylsulfates are preferred.

The nonionic surface active agents include, for example, fatty acid alkanolamides such as lauroyl diethanolamide, sucrose fatty acid esters such as sucrose mono and dilaurate, polyoxyethylene sorbitan fatty acid esters, polyoxyethylene fatty acid esters, polyoxyethylene hardened castor oil derivatives, lactose fatty acid esters, lactitol fatty acid esters, maltitol fatty acid esters, polyoxyethylene-polyoxypropylene block copolymers and the like. These agents may be used singly or in combination. These nonionic surface active agents can further improve the stability of the antibody.

The preferred blending amount of the anionic surface active agent is in the range of 0.5 to 3%, particularly 1 to 2% by weight of the composition and the preferred blending amount of the nonionic surface active agent is in the range of 0.1 to 5%, particularly 0.3 to 1.5% by weight of the composition. The weight ratio of the nonionic surface active agent and the anionic surface active agent is preferably in the range of 0.4:1 to 3:1, particularly 1:1 to 1.5:1.

Moreover, the oral composition of the present invention may further comprises 0.001 to 10% by weight of flavors including essential oils such as peppermint oil, spearmint oil and the like and flavoring materials such as l-menthol, carvone, eugenol, anethole and the like, preservative, sweeteners such as saccharin sodium, stevioside, neohesperidildihydrochalcone, glycyrrhizin, perillartine, p-methoxycinnamic aldehyde and the like, and proteins such as gelatine, peptone, casein, collagen, alubmin and the like. The addition of proteins can further improve the stability of the antibody. In the practice of the present invention, other effective ingredients may be additionally formulated in an effective amount, including mutanase, sorbic acid, alexidin, hinokitiol, cetylpyridinium chloride, alkylglycines, alkyldiaminoethyl glycine salts, allantoin, $\epsilon$-aminocaproic acid, tranexamic acid, azulene, vitamin E, water-soluble primary or secondary phosphates, quaternary ammonium compounds, sodium chloride, and crude drug extracts.

When the antibody is formulated in other types of composition, any other ingredients used for these compositions may be suitably added by ordinary techniques.

The oral composition of the present invention is not necessarily critical with respect to the pH and has preferably a pH of from 4 to 10, more preferably from 5 to 9, and most preferably from 5.5 to 7.5.

The composition of the present invention may be accommodated in a suitable container for practical service. For example, with toothpastes, there are used plastic containers such as plastic tubes, aluminum foil-laminated plastic tubes and the like, and metallic containers such as aluminum tubes. Although the antibody is relatively liable to deactivate in metallic containers, aluminum hydroxide used in combination can suitably prevent the deactivation of the antibody. Accordingly, the oral composition of the present invention may effectively be accommodated in metallic containers such as aluminum tubes.

The present invention is more particularly described by way of examples. Preparation of antisera, milks and antibodies used in Examples and Test Examples is first described.

PREPARATORY EXAMPLE (1) Preparation of Antigens

After *Bacteroides gingivalis* 381 (FERM BP-1027) is cultured in Todd-Hewitt broth containing hemin and menadione for two days, the grown bacteria are collected through centrifugation carried out at 800 rpm for 15 minutes. The thus collected bacteria, after being washed with 5 mM phosphate buffer of pH 7.4, were treated in 0.5% formalin overnight, thereby obtaining the whole cell antigen.

As to the preparation of the pilus antigen, after *Bacteriodes gingivalis* cultured for two days in the same manner as above is collected before being washed, the washed bacteria are gently stirred in distilled water containing glass beads for two days before being caused to pass through an No. 25 injection needle (0.5×25 mm) three times so as to sever the pili from the bacteria. The thus obtained solution is centrifuged at 8,000 rpm for 15 minutes to separate the bacteria from the pili contained in the supernatant, then the supernatant is dialyzed against distilled water before being lyophilized, thereby obtaining the pilus antigen. The yield is 0.0042% of the wet weight of the bacteria.

As to the capsule antigen, after bacteria collected in the same manner are allowed to react with phosphate buffer (0.05M, pH 7.4) containing 0.01M of EDTA at 60° C. for 30 minutes, the mixture solution is caused to pass through an No. 25 injection needle three times so as to separate the capsule from the bacteria. Next, the bacteria are removed by subjecting the thus obtained solution to centrifugation at 8,000 rpm for 15 minutes to obtain a supernatant which is then subjected to ultra-centrifugation at 40,000 rpm for two hours, thereby obtaining a deposit which is used as the capsule antigen. The yield is 0.09% of the wet weight of the bacteria.

Similarly, the whole cell antigen of *Bacteroides gingivalis* ATCC 33277 and its pilus and capsule antigens are prepared in the same manner as above. The yield of the pilus antigen is 0.0054% of the wet weight of the bacteria and the yield of the capsule antigen is 0.08% of the wet weight of the bacteria.

(2) Preparation of Antibodies

Serum antibodies are obtained by immunizing rabbits or pregnant sheep. Immunizations are carried out according to the usually adopted schedule. The initial immunization of rabbits with the whole cell antigen is carried out by subcutaneously injecting mixture consisting of Freund's complete adjuvant and 20 mg of bacterial cells. Following the subcutaneous injection, 10 mg of bacterial cells is injected in the vein of the ear of the animal four times every seven days for a total of 40 mg. The antiserum obtained is subjected to salting-out in 50% ammonium sulfate solution two times before being dialyzed against distilled water, thereby obtaining an antibody preparation. Antibody preparations for the pilus antigen were obtained by using 5 mg of the pilus antigen for the initial immunization and 10 mg of the pilus antigen for the subsequent immunization in the same manner as above. Antibody preparation for the capsule antigen are also obtained by using 10 mg of the capsule antigen for the initial preparation and 20 mg of the capsule antigen for the subsequent immunization in the same manner as above.

Milk antibody is obtained by immunizing a goat of two month pregnancy with the whole bacterial cell antigen. The initial immunization of the pregnant goat is carried out by subcutaneously injecting mixture consisting of Freund's complete adjuvant and 500 mg of bacterial cells, and other subcutaneous injections are carried out in the same manner 21 days and 28 days after the initial immunization. For the purpose of enhancing the production of the antibody contained in the milk, 500 mg of bacterial cells are orally administered 24 days after the initial administration. The milk is collected every day after the delivery. The collected milk is centrifuged at 15,000 rpm for one hour and the intermediate layer is collected. The thus collected layer is subjected to salting-out in 50% ammonium sulfate solution two times before being dialyzed against distilled water, thereby obtaining a goat's milk antibody preparation. Similarly, antibodies from the pilus antigen are prepared by using 50 mg of the pilus antigen for each immunization and antibodies from the capsule antigen are prepared by using 100 mg of the capsule antigen for each immunization.

EXAMPLE 1

A toothpaste of the following formulation was prepared.

| Abrasives | amounts indicated in Table 1 |
|---|---|
| 60% sorbitol solution | 35% by weight |
| Propylene glycol | 3.0 |
| Carrageenan | 1.0 |
| Gelatin | 0.3 |
| Saccharin sodium | 0.1 |
| Flavor | 1.0 |
| Sodium monofluorophosphate | 0.76 |
| Methylparaben | 0.2 |
| Butylparaben | 0.01 |
| Sodium laurylsulfate | 0.8 |
| Lauroyl diethanolamide | 1.0 |
| Anti-pilus antibody of rabbit against the strain of Bactroides gingivalis 381 | 0.5 |
| Water | balance |
| Total | 100.0% by weight |

This toothpaste is kept at 40° C. for 2 weeks, after which the antibody activity is measured according to the following method to determine a residual rate of the antibody. The results are shown in Table 1. It will be noted that the results are indicated by a relative activity in case where an antibody activity of a toothpaste using an aluminum hydroxide abrasive which is kept at 40° C. for 2 weeks is taken as 100.

Measurement of Antibody Activity:

Four milliliters of a phosphate buffer solution (0.1M, pH 7) is added to 1 g of the toothpaste so as to dissolve soluble components of the toothpaste in the phosphate buffer solution, followed by centrifugation to collct a supernatant liquid. The activity of the antibody in the supernatant liquid is determined by an ELISA method (Eng vall E. et al, J. Immunol., 109, 129–135, 1972) using *Bacteroides gingivalis* 381 strain as an antigen.

The activity of the antibody ingredient in an aluminum hydroxide-formulated toothpaste, which exhibited a maximum absorbance at 405 nm, is taken as 100%.

TABLE 1

| Abrasive | | Antibody |
|---|---|---|
| Kind | amount | Activity |
| aluminum hydroxide | 45% | 100 |
| calcium secondary phosphate dihydrate | 45 | 70 |
| calcium carbonate | 43 | 70 |
| silicic anhydride | 25 | 65 |

EXAMPLE 2

The same procedure as in Example 1 is repeated except that the anti-capsule antibody of goat against the strain of *Bacteroides gingivalis* ATCC 33277. The results of the antibody activity for the toothpastes using various abrasives were shown in Table 2.

TABLE 2

| Abrasive | | Antibody |
|---|---|---|
| Kind | amount | Activity |
| aluminum hydroxide | 45% | 100 |
| calcium secondary phosphate dihydrate | 45 | 68 |

TABLE 2-continued

| Abrasive | | Antibody |
|---|---|---|
| Kind | amount | Activity |
| calcium carbonate | 43 | 75 |
| silicic anhydride | 25 | 60 |

EXAMPLE 3

The effects of the antibodies on inhibiting the colonization of *Bacteroides gingivalis* 381 in hamster's mouth are examined.

Golden hamsters (male, 7 week age) are arranged in groups each consisting of six or seven head. After the manidibular first molars of the hamster are ligated with cotton thread (No. 50), 0.1 ml of a suspension in which $5 \times 10^8$ of *Bacteroides gingivalis* 381 per 1 ml of the suspension are suspended is inoculated in the mouth of the hamster. Thirty minutes later after the inoculation, 0.1 ml of a sample are injected in the mouth and the hamster's teeth are brushed twenty times with a interdental brush. The above operations are conducted for three consecutive days, and thereafter only the brushing operation are conducted twice a day. One week after the last inoculation, the ligation threads are removed. Then the number of *Bacteroides gingivalis* and the number of anaerobic bacteria contained in the ligation thread are determined.

As the sample, the equivalent mixture of each kind of antibodies against *Bacteroides gingivalis* 381 and glycerin, those consisting of the above-said equivalent mixture and protease, protease along, and the equivalent mixture of water and glycerin (control) are used. The concentration of protease was 0.01%.

The results are shown in Table 3.

TABLE 3

| | $\frac{\text{Number of Bacteroides gingivalis}}{\text{Number of anaerobic bacteria}} \times 100$ |
|---|---|
| Control | 7.14 ± 2.45 |
| Protease | 6.94 ± 3.39 |
| Rabbit anti-whole cell serum antibody | 2.17 ± 0.53 |
| Rabbit anti-whole cell serum antibody + Protease | 0.43 ± 0.11 |
| Rabbit anti-pilus serum antibody | 1.19 ± 0.30 |
| Rabbit anti-pilus serum antibody + Protease | 0.25 ± 0.06 |
| Rabbit anti-capsule serum antibody | 1.07 ± 0.31 |
| Rabbit anti-capsule serum antibody + Protease | 0.36 ± 0.08 |
| Goat anti-pilus milk antibody | 1.62 ± 0.42 |
| Goat anti-pilus milk antibody + Protease | 0.40 ± 0.07 |

EXAMPLE 4

| Toothpaste: | |
|---|---|
| propylene glycol | 3.0 by weight |
| sodium alginate | 0.9 |
| methylparaben | 0.1 |
| butylparaben | 0.01 |
| sodium benzoate | 0.2 |
| 60% sorbitol solution | 15.0 |
| 85% glycerine solution | 10.0 |
| saccharin sodium | 0.15 |
| sodium monofluorophosphate | 0.76 |
| dextranase (2,000,000 units/g) | 0.1 |
| gelatin | 0.3 |
| sodium laurylsulfate | 1.0 |
| flavor | 0.6 |
| aluminum hydroxide | 45.0 |
| horse anti-whole cell antibody against Bacteroides gingivalis 381 | 0.05 |
| purified water | balance |
| total | 100.0% by weight |

EXAMPLE 5

| Toothpaste: | |
|---|---|
| propylene glycol | 3.0% by weight |
| sodium carboxymethyl cellulose | 1.2 |
| methylparaben | 0.1 |
| butylparaben | 0.01 |
| sodium benzoate | 0.2 |
| 60% sorbitol solution | 35.0 |
| saccharin sodium | 0.15 |
| stannous fluoride | 0.41 |
| chlorhexidine hydrochloride | 0.01 |
| peptone | 0.2 |
| casein | 0.1 |
| sodium laurylsulfate | 0.8 |
| sucrose monolaurate | 1.0 |
| flavor | 0.6 |
| aluminum hydroxide | 45.0 |
| bovine anti-capsule antibody against Bacteroides gingivalis 381 | 0.02 |
| purified water | balance |
| total | 100.0% by weight |

EXAMPLE 6

| Toothpaste: | |
|---|---|
| propylene glycol | 2.5% by weight |
| carrageenan | 0.8 |
| methylparaben | 0.1 |
| butylparaben | 0.01 |
| sodium benzoate | 0.2 |
| 85% glycerine solution | 21.0 |
| saccharin sodium | 0.15 |
| sodium fluoride | 0.21 |
| collagen | 0.2 |
| albumin | 0.2 |
| sodium laurylsulfate | 0.8 |
| polyoxyethylene (20 moles) sorbitan monostearate | 0.8 |
| flavor | 0.6 |
| aluminum hydroxide | 45.0 |
| goat anti-pilus antibody against Bacteroides gingivalis ATCC 33277 | 0.5 |
| purified water | balance |
| total | 100.0% by weight |

EXAMPLE 7

| Toothpaste: | |
|---|---|
| propylene glycol | 2.5% by weight |
| carrageenan | 1.0 |
| methylparaben | 0.1 |
| butylparaben | 0.01 |
| sodium benzoate | 0.2 |
| 60% sorbitol solution | 30.0 |
| saccharin sodium | 0.15 |
| sodium monofluorophosphate | 0.21 |
| chlorhexidine hydrochloride | 0.01 |

| Toothpaste: | |
| --- | --- |
| sodium laurylsulfate | 0.2 |
| sodium lauroylsarcosinate | 0.8 |
| polyoxyethylene (60 moles) hardened castor oil | 0.8 |
| flavor | 0.6 |
| aluminum hydroxide | 45.0 |
| rabbit anti-pilus antibody against Bacteroides gingivalis 381 | 0.1 |
| purified water | balance |
| total | 100.0% by weight |

What is claimed is:

1. A method for stabilizing an antibody against deactivation in a dentifrice composition containing an anionic surface active agent, said antibody having been obtained by immunizing a mammal with at least one antigen selected from the group consisting of periodontal causative bacteria, pilus fractions thereof and capsule fractions thereof comprising combining aluminum hydroxide with said antibody in an amount sufficient to stabilize said antibody.

2. The method of claim 1, wherein the antibody, which is separated from an antiserum or milk obtained by immunizing the mammal with said antigen, is blended in the composition.

3. The method of claim 1, wherein an antiserum or milk, which is obtained by immunizing the mammal with said antigen, is blended as the antibody in the composition.

4. The method of claim 1, wherein the causative bacteria are gram-negative bacteria in the mouth.

5. The method of claim 4, wherein said gram-negative bacteria are those of *Bacteroides gingivalis* or *Antinobacillus actinomyceyemcomitans*.

6. The method of claim 1, wherein said causative bacteria are those of *Antinomyces viscosus*.

7. The method of claim 1, wherein said antibody is contained in an amount of from 0.0002 to 10% by weight of the composition.

8. The method of claim 1, wherein said aluminum hydroxide is contained in an amount of from 5 to 70% by weight of the composition.

9. The method of claim 1, wherein said antibody is contained in an amount of from 0.0002 to 5% by weight of the composition.

10. The method of claim 1, wherein in said aluminum hydroxide is contained in an amount of from 10 to 55% by weight of the composition.

11. The method of claim 1, wherein the dentifrice is a toothpaste, a toothpowder, or a liquid dentifrice.

12. A method for stabilizing an antibody against deactivation in a dentifrice composition containing an anionic surface active agent, said antibody having been obtained by immunizing a mammal with at least one antigen selected from the group consisting of *Bacteroides gingivalis*, pilus fractions thereof and capsule fractions thereof comprising combining aluminum hydroxide with said antibody in an amount sufficient to stabilize said antibody.

13. The method of claim 12, wherein the antigen is *Bacteroides gingivalis*.

14. A method for stabilizing an antibody against deactivation in a dentifrice composition containing an anionic surface active agent, said antibody having been obtained by immunizing a mammal with at least one antigen selected from the group consisting of *Antinobacillus actinomycetemcomitans*, pilus fractions thereof and capsule fractions thereof comprising combining aluminum hydroxide with said antibody in an amount sufficient to stabilize said antibody.

15. The method of claim 14, wherein the antigen is *Antinobacillus antinomycetemcomitans*.

* * * * *